United States Patent [19]

Arndt et al.

[11] 4,242,275

[45] Dec. 30, 1980

[54] PROCESS FOR THE PREPARATION OF ISOMER-FREE TOLUENE-4-SULFONIC ACID

[75] Inventors: Otto Arndt, Hofheim am Taunus; Bernhard Mees, Ehlhalten, both of Fed. Rep. of Germany

[73] Assignee: Hoechst Aktiengesellschaft, Frankfurt am Main, Fed. Rep. of Germany

[21] Appl. No.: 100,462

[22] Filed: Dec. 5, 1979

Related U.S. Application Data

[63] Continuation of Ser. No. 950,582, Oct. 12, 1978, abandoned, which is a continuation of Ser. No. 769,037, May 11, 1977, abandoned.

[51] Int. Cl.$^3$ ............................................. C07C 143/24
[52] U.S. Cl. .................................................. 260/505 E
[58] Field of Search .................................... 260/505 E

[56] References Cited

U.S. PATENT DOCUMENTS 1,311,848  7/1919  Lepers ................................. 260/505

FOREIGN PATENT DOCUMENTS 371212  1/1973  U.S.S.R. ................................. 260/505

OTHER PUBLICATIONS

Gilbert, "Sulf. & Related Reactions" (1965), pp. 71, 72.

*Primary Examiner*—Alan Siegel
*Attorney, Agent, or Firm*—Curtis, Morris & Safford

[57] ABSTRACT

Pure toluene-4-sulfonic acid is obtained without forming any by-products by sulfonating toluene with sulfuric acid at an elevated temperature, separating a first batch of toluene-4-sulfonic acid hydrate, washing it free of isomers with sulfuric acid, combining the mother liquor and the washing effluent, heating them, allowing a second batch of hydrate to crystallize and, optionally, working up the final mother liquor by hydrolizing the toluene sulfonic acids therein and recycling the toluene so formed and the sulfuric acid after concentrating it to its initial strength.

25 Claims, No Drawings

PROCESS FOR THE PREPARATION OF ISOMER-FREE TOLUENE-4-SULFONIC ACID

This is a continuation of application Ser. No. 950,582, filed Oct. 12, 1978, now abandoned, which was a continuation of application Ser. No. 769,037 filed May 11, 1977, now abandoned.

The present invention relates to a process for the preparation of isomer-free toluene-4-sulfonic acid. In the following all percentages are by weight unless otherwise stated.

In the sulfonation of toluene with sulfuric acid, about 15% of toluene-2- and -3-sulfonic acids are obtained besides toluene-4-sulfonic acid. The separation of these isomers is extremely complicated. For this reason, the sulfonation of toluene has already been carried out with sulfur trioxide in sulfur dioxide (U.S. Pat. No. 2,828,333), which process yields, when carried out in an appropriate manner, a mixture with a content of 92.5% of toluene-4-sulfonic acid, 3.5% of toluene-2-sulfonic acid and 1% of sulfone. Due to the cooling and recovery measures for the sulfur dioxide, this process is rather complicated from the technical point of view; moreover, a separation of the by-products is also required.

It is known that the undesired formation of toluene-2-sulfonic acid can be controlled by increasing the temperature, reducing the sulfonic acid concentration and by the presence of toluene-4-sulfonic acid in the aqueous sulfuric acid phase. It is assumed that with the reaction proceeding between toluene and sulfuric acid, the toluene-4-sulfonic acid concentrating in the sulfuric acid phase effects a reduction of the proportion of toluene-2-sulfonic acid. However, the concentration values for toluene-2-sulfonic acid mentioned for this process are not less than 15% (Rec. trav. chim. Pays-Bas 82 (1963) 659, 83, (1964) 226).

Furthermore, it is known that toluene-3-sulfonic acid represents the isomer that is most thermostable (Proc. Chem. Soc. 1963, 174).

It is, therefore, surprising that in a simple two-step process the sulfonation of toluene with sulfuric acid can be effected in a way that the proportion of toluene-4-sulfonic acid rises to more than 90%.

Thus, the present invention provides a process for the preparation of toluene-4-sulfonic acid by sulfonating toluene in sulfuric acid, which comprises sulfonating at first toluene with sulfuric acid of at least 85% strength at a temperature of up to about 140° C., adjusting the sulfuric acid concentration, if necessary, to 60 to 75%, allowing the toluene-4-sulfonic acid to crystallize in the form of its hydrate, isolating said hydrate, washing it free of isomers with aqueous sulfuric acid, combining the mother liquor separated from said hydrate with the aqueous sulfuric acid effluent from the washing, heating them to a temperature in the range of from 120° to 160° C., allowing the toluene-4-sulfonic acid to crystallize in the form of its hydrate by cooling, isolating the hydrate, optionally working up the filtrate by hydrolyzing the toluene-sulfonic acids contained therein, and recycling the toluene thus obtained as well as, optionally, the sulfuric acid after its regeneration into the process.

In the following, some appropriate embodiments of the process of the invention have been described in detail:

The sulfonation is effected preferably at a temperature of more than 110° C., especially in the range of from 115° to 125° C. The sulfuric acid contains preferably from 0 to 10%, especially from 4 to 8% of water and is used preferably in an excess amount of from, for example, 2 molar equivalents.

The toluene may be introduced in the gaseous state, however, preferably used in the liquid state, the sulfuric acid and the toluene being combined advantageously in the same ratio as they react with each other.

The isolation of the toluene-sulfonic acid hydrate is achieved most easily with a sulfuric acid concentration in the range of from 60 to 75%, which is optionally adjusted by diluting the sulfuric acid. If the sulfonation is carried out at the preferred temperatures mentioned above, the reaction mixture is cooled for the crystallization of the hydrate.

In this first step, about 60 to 75% of the theoretical amount of toluene-4-sulfonic acid hydrate are obtained, in which process an amount preferably not exceeding about 67% of hydrate is allowed to crystallize, in order to obtain a product which can be filtered easily.

The isolated hydrate of this first reaction step is washed until it is free of isomers, while using aqueous sulfuric acid of from 60 to 80%, especially 80% strength, suitably in the smallest possible amount, and the product is isolated.

The filtrate, combined with the sulfuric acid effluent from the washing, is heated to a temperature in the range of from 120° to 160° C., especially 140° C., and this temperature is maintained for a certain time, preferably for about 45 to 90 minutes. Thereafter the mixture is cooled to a degree that the toluene-4-sulfonic acid crystallizes in the form of its hydrate, as quantitatively as possible, and this second fraction is isolated. An amount of from 10 to 25% of the theoretical amount of the hydrate is obtained, so that the total yield is at least 90% of consistent quality.

The isomeric toluene-sulfonic acids remaining in the filtrate of this second reaction step are hydrolized quantitatively into toluene and sulfuric acid in a stripping process. In this process a minor part of this filtrate is preferably introduced at 185° C., and the remaining part, which has been diluted with water, is added in the same ratio as the toluene is distilled off. Instead of diluting with water, steam may also be blown into the reaction mixture. In this manner, about 9% of the theory of toluene are recovered, which is recycled into the sulfonation process. The yield of toluene-4-sulfonic acid is thus increased to more than 95% of the theory, calculated on consumed toluene.

The sump sulfuric acid is brought to a content of from about 80 to 85% of $H_2SO_4$ by distilling off water (up to a partial pressure of from about 190 to 200 torr at 185° C.), and is optionally adjusted to the original sulfuric acid concentration—suitably with "oleum" (fuming sulfuric acid)—, in order to ensure a stationary operation. The higher concentration is suitably effected with the use of oleum of from 50 to 100% strength, especially with 65% oleum.

There occurs no accumulation of toluene-disulfonic acids. In order to avoid a concentration of organic impurities in the sump sulfuric acid, a minor portion of up to about 10% may be eliminated as waste sulfuric acid. The content of organic impurities can be destroyed by way of oxidation, for example in a Pauling plant.

In the process balance, only toluene and oleum are therefore indicated as starting substances. An isomer-free toluene-4-sulfonic acid is obtained in a high yield and without by-products. Thus, the process of the invention is superior to the known processes from an economical and ecological point of view.

Toluene-4-sulfonic acid is a precursor for dyestuffs, pesticides and surface-active substances. For further processing the purity of this starting material is of considerable importance, since a content of isomeric toluene-sulfonic aicds in the further chemical reactions results necessarily in by-products and thus in a deteriorated quality of the product and a reduced yield.

The following Example illustrates the invention, the parts being by weight.

EXAMPLE

1150 Parts of 65% oleum are introduced, while stirring and cooling, into 2100 parts of a sulfuric acid recovered from the process under operation (containing 1680 parts of $H_2SO_4$, 336 parts of water and 4% of organic impurities). 992 Parts of toluene (839 parts of fresh toluene and 83 parts of regenerated toluene) are introduced within 30 minutes at 115° C., while stirring and refluxing, into the sulfuric acid thus obtained which contains 6% of water. A stoichiometrical analysis was performed independently of the test described in this Example and was based on the data presented therein. For purposes of the analysis, complete reaction of toluene and sulfuric acid was assumed. The above reaction was calculated to consume 980 parts of sulfuric acid and form 180 parts of water leaving 2014 parts of sulfuric acid, 349 parts of water, and 84 parts of organic impurities.

By adding 250 parts of water and cooling to 30° C., toluene-4-sulfonic acid crystallizes in the form of its hydrate and is filtered off. The same stoichiometrical analysis as described above shows that the sulfuric acid concentration has been adjusted to 74.5% by weight based on the sulfuric acid, water, and organic impurities. The residue is washed with 400 parts of 80% sulfuric acid. The crystallized product contains 1150 parts of toluene-4-sulfonic acid.

The filtrate combined with the sulfuric acid recovered from the washing is heated to 140° C. and is maintained at this temperature for 1 hour. It is then cooled, and the crystallized hydrate of the toluene-4-sulfonic acid is filtered off at 10° C. The crystallized product contains 380 parts of toluene-4-sulfonic acid.

The total yield of isomer-free toluene-4-sulfonic acid is 97% of the theory, calculated on starting (fresh) toluene.

The second filtrate sulfuric acid is diluted with 800 parts of water, 10% of this mixture are heated to 185° C., and the rest is introduced at this temperature within 5 hours. Subsequently the toluene is separated by means of steam. 83 Parts of regenerated toluene are obtained.

The pressure is reduced to 195 torr, snd 400 parts of water are distilled off. The mixture is clarified from separated charcoal, and 2300 parts of 80% sulfuric acid are obtained which contains 1.5% of organically bound carbon. Of this acid, 2100 parts are recycled into the process, and about 200 parts are eliminated as waste sulfuric acid.

We claim:

1. A process for the preparation of toluene-4-sulfonic acid, which comprises heating toluene with sulfuric acid of at least 85% by weight strength to a temperature of up to 140° C.; crystallizing toluene-4-sulfonic acid formed in the form of its hydrate, said crystallizing being effected by cooling the reaction mixture if the heating is effected at a temperature of more than 110° C.; isolating said hydrate; washing it free of isomers with aqueous sulfuric acid; combining the mother liquor separated from said hydrate with the aqueous sulfuric acid used in said washing; heating these at a temperature of from 120° to 160° C. for a time sufficient to form additional toluene-4-sulfonic acid; cooling the combination of mother liquor and aqueous sulfuric acid to crystallize the toluene-4-sulfonic acid in the form of its hydrate; and isolating the hydrate.

2. A process for the preparation of toluene-4-sulfonic acid, which comprises heating toluene with sulfuric acid of at least 85% by weight strength to a temperature of up to 140° C.; crystallizing toluene-4-sulfonic acid formed in the form of its hydrate, said crystallizing being effected by cooling the reaction mixture if the heating is effected at a temperature of more than 110° C.; isolating said hydrate; washing it free of isomers with aqueous sulfuric acid; combining the mother liquor separated from said hydrate with the aqueous sulfuric acid used in said washing; heating these in a separate reaction step at a temperature of from 120° to 160° C. for a time sufficient to form additional toluene-4-sulfonic acid; cooling the combination of mother liquor and aqueous sulfuric acid to crystallize the toluene-4-sulfonic acid in the form of its hydrate; and isolating the hydrate.

3. A process for the preparation of toluene-4-sulfonic acid, which comprises heating toluene with an excess amount of two molar equivalents of sulfuric acid of at least 85% by weight strength to a temperature of up to 140° C.; crystallizing toluene-4-sulfonic acid formed in the form of its hydrate, said crystallizing being effected by cooling the reaction mixture if the heating is effected at a temperature of more than 110° C.; isolating said hydrate; washing it free of isomers with aqueous sulfuric acid; combining the mother liquor separated from said hydrate with the aqueous sulfuric acid used in said washing; heating these at a temperature of from 120° to 160° C. for a time sufficient to form additional toluene-4-sulfonic acid; cooling the combination of mother liquor and aqueous sulfuric acid to crystallize the toluene-4-sulfonic acid in the form of its hydrate; and isolating the hydrate.

4. A process as claimed in claim 1, wherein the sulfuric acid of at least 85% by weight strength contains 0 to 10% by weight of water.

5. A process as claimed in claim 1, wherein the sulfuric acid of at least 85% by weight strength contains 4 to 8% by weight of water.

6. A process as claimed in claim 1, wherein the sulfuric acid of at least 85% by weight strength is added in excess.

7. A process as claimed in claim 1, wherein following its heating with toluene, the concentration of the sulfuric acid is adjusted to 60 to 75% by weight based on its acid, water and organic impurities content.

8. A process as claimed in claim 1, wherein a part of the final mother liquor obtained by isolating the second hydrate crystal fraction is heated to about 185° C. whereby the toluene sulfonic acids are split into toluene and sulfuric acid, and the rest of said mother liquor is added together with water or steam at a ratio as the toluene formed distils off.

9. A process as claimed in claim 1, wherein the starting materials are heated to a temperature above 110° C.

10. A process as claimed in claim 1, wherein the starting materials are heated to a temperature of 115° to 125° C.

11. A process as claimed in claim 1, wherein an excess of about 2 mols of sulfuric acid are added per mol of toluene.

12. A process as claimed in claim 1, wherein the toluene is liquid.

13. A process as claimed in claim 1, wherein liquid toluene and sulfuric acid are added at the same rate at they are consumed in the reaction.

14. A process as claimed in claim 1, wherein the first fraction of said hydrate is allowed to crystallize while cooling.

15. A process as claimed in claim 1, wherein the first crystallization step is stopped when about 67% of the theoretical amount of hydrate have separated.

16. A process as claimed in claim 1, wherein the hydrate is washed with sulfuric acid having a concentration of 60 to 80% by weight.

17. A process as claimed in claim 16, wherein the concentration is 80%.

18. A process as claimed in claim 1, wherein the temperature is 140° C.

19. A process as claimed in claim 18, wherein the temperature is maintained in said range for 45 to 90 minutes.

20. A process as claimed in claim 8, wherein the sulfuric acid is concentrated by distillation to 80 to 85% by weight.

21. A process as claimed in claim 20, wherein the concentrated acid is adjusted to the initial concentration by adding fuming sulfuric acid.

22. A process as claimed in claim 21, wherein the fuming sulfuric acid contains 50 to 100% of free sulfur trioxide.

23. A process as claimed in claim 22, wherein the content is 65%.

24. A process as claimed in claim 8, wherein the toluene is recycled into the process of claim 1.

25. A process as claimed in claim 21, wherein the sulfuric acid so-obtained is recycled into the process of claim 1.

* * * * *

UNITED STATES PATENT AND TRADEMARK OFFICE
CERTIFICATE OF CORRECTION

PATENT NO. : 4,242,275
DATED : December 30, 1980
INVENTOR(S) : Arndt et al.

It is certified that error appears in the above-identified patent and that said Letters Patent are hereby corrected as shown below:

In the Heading, insert

--[30] Foreign Application Priority Data

May 13, 1976    Germany    2621168 --.

Signed and Sealed this

Tenth Day of March 1981

[SEAL]

Attest:

RENE D. TEGTMEYER

Attesting Officer    Acting Commissioner of Patents and Trademarks